(12) United States Patent
Karlsson et al.

(10) Patent No.: US 11,255,852 B2
(45) Date of Patent: Feb. 22, 2022

(54) METHOD TO DETERMINE SOLVENT CORRECTION CURVES

(71) Applicant: CYTIVA SWEDEN AB, Uppsala (SE)

(72) Inventors: Olof Karlsson, Uppsala (SE); Henrik Berling, Uppsala (SE)

(73) Assignee: CYTIVA SWEDEN AB, Uppsala (SE)

( * ) Notice: Subject to any disclaimer, the term of this patent is extended or adjusted under 35 U.S.C. 154(b) by 585 days.

(21) Appl. No.: 15/519,238

(22) PCT Filed: Oct. 26, 2015

(86) PCT No.: PCT/EP2015/074768
§ 371 (c)(1),
(2) Date: Apr. 14, 2017

(87) PCT Pub. No.: WO2016/066591
PCT Pub. Date: May 6, 2016

(65) Prior Publication Data
US 2017/0242001 A1    Aug. 24, 2017

Related U.S. Application Data (60) Provisional application No. 62/072,574, filed on Oct. 30, 2014.

(51) Int. Cl.
*G01N 33/50* (2006.01)
*G01N 33/543* (2006.01)
(Continued)

(52) U.S. Cl.
CPC ..... *G01N 33/54373* (2013.01); *G01N 21/554* (2013.01); *G01N 21/648* (2013.01);
(Continued)

(58) Field of Classification Search
CPC .. G01N 21/554; G01N 21/648; G01N 33/483; G01N 33/5302; G01N 33/54353;
(Continued)

(56) References Cited

U.S. PATENT DOCUMENTS

| | | | |
|---|---|---|---|
| 2002/0098528 A1 | 7/2002 | Gordon et al. | |
| 2004/0048323 A1* | 3/2004 | Boga | G01N 33/54306 435/7.93 |

(Continued)

FOREIGN PATENT DOCUMENTS

| | | |
|---|---|---|
| CN | 1636138 A | 7/2005 |
| CN | 1894586 A | 1/2007 |

(Continued)

OTHER PUBLICATIONS

"Biacore (TM) Assay Handbook", 29-0194-00 Edition AA; General Electric Company; Jan. 1, 2012; pp. 1-74.
(Continued)

*Primary Examiner* — Christopher L Chin
(74) *Attorney, Agent, or Firm* — Jeff B. Vockrodt; Culhane Meadows, PLLC

(57) ABSTRACT

In one embodiment, the present invention relates to a method for establishing a solvent correction curve as well as using the curve for obtaining a corrected sensorgram or corrected report points from a sensorgram of an analyte. In another embodiment, the present invention provides an analytical system for studying molecular interactions, which comprises computer processing means including program code means for performing the steps of the methods. Also provided is a computer program product comprising program code means stored on a computer readable medium or carried on an electrical or optical signal for performing the steps of the methods.

12 Claims, 4 Drawing Sheets

(51) Int. Cl.
*G01N 33/53* (2006.01)
*G01N 33/483* (2006.01)
*G01N 21/552* (2014.01)
*G01N 21/64* (2006.01)
*B01L 3/00* (2006.01)
*B01F 13/00* (2006.01)

(52) U.S. Cl.
CPC ....... *G01N 33/483* (2013.01); *G01N 33/5302* (2013.01); *G01N 33/54353* (2013.01); *B01F 13/0094* (2013.01); *B01L 3/5027* (2013.01); *B01L 3/502715* (2013.01)

(58) Field of Classification Search
CPC ............. G01N 33/54373; B01L 3/5027; B01L 3/502715; B01F 13/0094
USPC ............. 422/82.11; 435/288.7; 436/525, 805
See application file for complete search history.

(56) References Cited

U.S. PATENT DOCUMENTS

| | | | |
|---|---|---|---|
| 2004/0252584 A1* | 12/2004 | Ji | B01F 5/0646 366/341 |
| 2006/0068490 A1* | 3/2006 | Tang | B01F 5/0603 435/287.2 |
| 2012/0264233 A1* | 10/2012 | Jansson | B01F 13/0072 436/501 |

FOREIGN PATENT DOCUMENTS

| | | |
|---|---|---|
| CN | 101517413 A | 8/2009 |
| JP | 2005134187 A | 5/2005 |
| JP | 3787578 B2 | 6/2006 |

OTHER PUBLICATIONS

English Translation of CN Office Action for corresponding application No. 201580059042.5, dated Dec. 13, 2018; 12 pages.

China Second Office Action and Supplementary Search Report corresponding to Chinese Application No. 201580059042.5, dated Aug. 27, 2019.

GE Healthcare Life Sciences: "Biocore (TM) Assay Handbook", Jan. 1, 2012, General Electric Company, Piscataway, NJ USA, pp. 1-74.

Ewart, "Mixing in microchannels", Jun. 1, 2004, Imperial College, London, pp. 1-86.

International Search Report and Written Opinion regarding International Application No. PCT/EP2015/07468, dated Apr. 4, 2016, 16 pages.

* cited by examiner

METHOD TO DETERMINE SOLVENT CORRECTION CURVES

CROSS-REFERENCE TO RELATED APPLICATIONS

This application is a filing under 35 U.S.C. 371 of international application number PCT/EP2015/074768, filed Oct. 26, 2015, which claims priority to U.S. application No. 62/072,574, filed Oct. 30, 2014, the entire disclosures of each of which are hereby incorporated by reference in their entireties.

FIELD OF THE INVENTION

The present invention relates to a method for adjusting bulk signal mismatches between active and reference detection surfaces. More specifically, the invention relates to a method for establishing a solvent correction curve as well as using the curve for obtaining a corrected sensorgram or corrected report points from a sensorgram of an analyte. The invention also relates to an analytical system and a computer program product for performing steps of the method.

BACKGROUND OF THE INVENTION

Analytical sensor systems (i.e., label-free systems) that can monitor molecular interactions in real time are gaining increasing interest. These systems are often based on optical biosensors and usually referred to as interaction analysis sensors or biospecific interaction analysis sensors. A representative biosensor system is the Biacore® instrumentation sold by GE Healthcare Life Sciences, which uses surface plasmon resonance (SPR) for detecting interactions between molecules in a sample and molecular structures immobilized on a sensing surface. With the Biacore® systems it is possible to determine in real time without the use of labeling not only the presence and concentration of a particular molecule in a sample, but also additional interaction parameters such as, for instance, the association rate and dissociation rate constants for the molecular interaction. The apparatus and theoretical background are fully described in the literature (see e.g., Jonsson, U., et al., BioTechniques 11: 620-627 (1991)). Normally, the technique involves the immobilization of a ligand to the special optical sensor surface of a sensor chip (flow cell), contacting the sensor chip with a flow of sample containing the analyte of interest, and then measuring the change in the surface optical characteristics of the sensor chip arising from the binding between the ligand and the analyte. For further details on SPR, reference is also made to U.S. Pat. Nos. 5,313,264, 5,573,956 and 5,641,640.

When running assays with analyte molecules that are slightly hydrophobic, inclusion of an organic solvent in the running buffer and samples may be necessary. For smaller organic molecule analytes (80-1000 Da), an organic solvent such as 2-5% dimethyl sulphoxide (DMSO) is typically used. Many of these applications are dependent on reference subtraction between the active surface and a reference surface in order to get enough data quality. However, bulk signals (from differences in refractive index in running buffer and samples) are not completely quenched by reference subtraction, depending on the amount of ligand immobilized on the active surface. This is added to the response from analyte binding and since the mismatch also varies with pipetting errors it can span from significant positive to negative values. This may be fatal for the data quality in assays depending on report point readouts.

However, this can be corrected for by measuring the referencing error as a function of bulk response in the reference and than adjusting every sample by that function, i.e. solvent correction. When performing solvent correction the user has to prepare a number of solutions (eight according to the recommended procedure for Biacore) with representative bulk responses. These solutions are injected over every reference-active detection surface pair in order to establish correction curves. Since the procedure is repeated throughout the run at least one time and since there is no means to use the same position for multiple times the plate occupancy and user workload is significant.

There is a need to simply and automate the solvent correction process.

BRIEF SUMMARY OF THE INVENTION

The present invention relates to a method for establishing a solvent correction curve as well as using the curve for obtaining a corrected sensorgram or corrected report points from a sensorgram of an analyte.

In one aspect, it provides a method for establishing a solvent correction curve, which comprises
   a. providing a first solution comprising a high concentration of an organic solvent and a second solution comprising a low concentration of the same organic solvent;
   b. mixing the two solutions on line at a predetermined proportion in a flow channel of an integrated microfluidic cartridge (IFC), which flow channel comprises a flow cell with an optical sensor surface that is not immobilized with a ligand or analogue;
   c. obtaining a sensorgram of the mixed solution from the optical sensor surface of step (b), the sensorgram comprising a report point at a stable section of the sensorgram;
   d. mixing the two solutions on line at the same predetermined proportion as in step (b) in another flow channel of the integrated microfluidic cartridge (IFC), which flow channel comprises a flow cell with an optical sensor surface that is immobilized with a ligand or analogue;
   e. obtaining a sensorgram of the mixed solution from the optical sensor surface of step (d), the sensorgram comprising a report point at a stable section of the sensorgram;
   f. repeat steps (b) and (c) n times each at a different, predetermined proportion of the two solutions; and
   g. establishing a solvent correction curve using the report points;
wherein n is at least 3.

In another aspect, it provides a method for obtaining a corrected response of an analyte, which comprises
   a. generating a sensorgram for a solution with the analyte in a flow cell including an optical sensor surface which contains immobilized partners for the analyte;
   b. generating a sensorgram for the solution in the same or another flowcell having an optical sensor surface which does not contain immobilized partners for the analyte;
   c. obtaining a corrected response by first, for each signal, deducting the signal of (b) from that of (a) to generate a modified sensorgram, followed by adjusting signals of the modified sensorgram or report points from the sensorgram according to the correction curve obtained through certain embodiments of the invention.

In yet another aspect, it provides a method for mixing two liquids in a microchannel, which comprises
   a. providing a first liquid comprising a specific composition and a second liquid comprising another composition;
   b. mixing the two liquids on line at a predetermined proportion in a micochannel;
wherein mixing the two liquids comprises injecting the two liquids each at an individual, preset flow rate, let the combined liquid travel through the microchannel, and reverse the flow so that the combined liquid passes through the microchannel a second time.

In another aspect, the present invention provides an analytical system for studying molecular interactions, which comprises computer processing means including program code means for performing the steps of the methods.

In still another aspect, the present invention provides a computer program product comprising program code means stored on a computer readable medium or carried on an electrical or optical signal for performing the steps of the methods.

Further details and advantages of the present invention will appear from the description and claims below.

BRIEF DESCRIPTION OF THE DRAWINGS

FIGS. 1 A and B illustrates details of a portion of an IFC as two solutions are mixed three times, showing the direction (arrows) and mix pattern in the flow channels.

DETAILED DESCRIPTION OF THE INVENTION

Small molecule applications are increasingly done using a label-free system. As discussed above, these applications are typically dependent on solvent correction which requires a significant amount of hands-on time, is error prone and occupies a significant number of reagent/sample positions in the instrument. These issues are worsened for systems with multi-channel configurations. Embodiments of the invention significantly reduce the amount of user effort and position occupation, as compared to manual operation. Embodiments of the invention is especially useful for assays using an integrated microfluidic cartridge (IFC) having parallel channels, i.e., the so-called multi-channel systems.

The invention relates to novel methods for establishing a solvent correction curve, as well as methods for obtaining a corrected response of an analyte. The invention further relates to an analytical system and a computer program product for performing steps of the method.

Thus, in one aspect, the present invention relates to a method for establishing a solvent correction curve, comprising
   a. providing a first solution comprising a high concentration of an organic solvent and a second solution comprising a low concentration of the same organic solvent;
   b. mixing the two solutions on line at a predetermined proportion in a flow channel of an integrated microfluidic cartridge (IFC), which flow channel comprises a flow cell with an optical sensor surface that is not immobilized with a ligand or analogue;
   c. obtaining a sensorgram of the mixed solution from the optical sensor surface of step (b), the sensorgram comprising a report point at a stable section of the sensorgram;
   d. mixing the two solutions on line at the same predetermined proportion as in step (b) in another flow channel of the integrated microfluidic cartridge (IFC), which flow channel comprises a flow cell with an optical sensor surface that is immobilized with a ligand or analogue;
   e. obtaining a sensorgram of the mixed solution from the optical sensor surface of step (d), the sensorgram comprising a report point at a stable section of the sensorgram;
   f. repeat steps (b) and (c) n times each at a different, predetermined proportion of the two solutions; and
   g. establishing a solvent correction curve using the report points;
wherein n is at least 3.

In certain embodiments, when n is three, the predetermined proportion includes 1:0 (100% of the first solution and no second solution); 0:1 (100% of the second solution and no first solution); and a mixing of the first and the second solution, such as at a 0.5:0.5 ratio. In certain embodiments, the predetermined proportions are spaced between 1:0 and 0:1. In certain preferred embodiments, the predetermined proportions are evenly spaced between 1:0 and 0:1.

In certain embodiments, the report point is placed a specified time after the start of the injection. Preferably, the time is the same for all injection of the same type. In addition, a baseline report point is placed at a specified time before the injection or a series of injections. The response used here is the difference between these two; called relative response.

For the correction curve the sensorgram from the immobilized flow cell is subtracted with the sensorgram from the reference (not immobilized), the relative report points response gives the y-axis value. The same relative report point value from the reference sensorgram gives the x-axis value. When more than 3 points are plotted, a solvent correction curve may be generated by for example, fitting the points to a $2^{nd}$ degree polynom.

When samples are run the reference response is used as the x-value that gives a correction number from the y-axis, this number is added to the relative response of the reference subtracted sample response to give the corrected response.

In certain embodiments, mixing the two solutions comprises injecting the two solutions each at an individual, preset flow rate, let the combined solution travel through the flow cell(s), and reverse the flow so that the combined solution passes through the flow cell(s) a second time. Optionally, the flow may be reversed another time so that the combined solution passes through the flow cell(s) a third time.

In certain embodiments, mixing the two solutions comprises injecting the two solutions each at an individual, preset flow rate, let the combined solution travel through a channel(s) and/or valve(s), prior to entering the flow cell.

In certain embodiments, mixing the two solutions is realized by controlling flow rate for each solution.

In certain embodiments, the flow rates of the solutions are controlled by one or more pumps. In certain embodiments, one of the solutions may be controlled by a pump, while the other solution may be introduced by aspiration by needle. In some embodiments, a second pump is present at the other side of the flow cell, the two pumps act in concert to moving the solutions across the flow cell.

In certain embodiments, the integrated microfluidic cartridge comprises multiple, parallel channels.

In certain embodiments, the organic solvent is a solvent that has a refractive index different from the main component of the buffer (e.g., water). In certain embodiments, the organic solvent is DMSO or glycerol. The concentration of the organic solvent in the first and second solution is chosen such that it covers a range that corresponds to the solvent mismatch between the samples and the running buffer. In some embodiments, the concentration of the organic solvent in the first and second solution may be +/−50% of the range, +/−40% of the range, +/−30% of the range or +/−20% of the range. For example, when the potential solvent mismatch between the sample and the running buffer is about 2%, the first solution may have a concentration of the organic solvent at 3%, the second solution may have a concentration of the organic solvent at 1%.

In another aspect, the present invention relates to a method for obtaining a corrected response of an analyte, comprising
- a) generating a sensorgram for a solution with the analyte in a flow cell including an optical sensor surface which contains immobilized partners for the analyte;
- b) generating a sensorgram for the same solution in the same or another flowcell including an optical sensor surface which does not contain immobilized partners for the analyte;
- c) obtaining a corrected response by first, for each signal, deducting the signal of (b) from that of (a) to generate a modified sensorgram, followed by adjusting signals of the modified sensorgram or corrected report points from the sensorgram according to the correction curve obtained by certain embodiments of the invention.

In certain embodiments, an analyte may be any macromolecular particle, such as a chemical compound or a biological molecule in the solution. The macromolecular particle may, for example, be a protein, a polysaccharide, a nucleic acid molecule. In certain preferred embodiments, the analyte is a small molecule. In certain embodiments, the analyte is a small molecule having a size of between about 80 to about 1000 Dalton.

In certain embodiments, a ligand or an analogue thereof is used herein in its conventional meaning for an entity comprising a functional group capable of interaction with an analyte a target compound. Examples of groups of ligands are positively charged groups (anion exchange ligands); negatively charged groups (cation exchange ligands); hydrophobic groups; groups with an affinity for a specific target compound, such as the affinity of an antigen for an antibody (affinity ligands); etc.

Thus, using merged injection within the IFC and improving sample mixing by reversing the flow (i.e., streaming the sample back over the detection spot), an improved method for establishing a solvent correction curve is established through repeating the procedure with varying mixing proportions between two extreme solutions. To generate an accurate solvent correction curve, at least 4 report points from different concentrations of the organic solvent solution are needed. Preferably, a solvent correction curve includes eight or more report points.

Solvent correction curve: The SPR signal reflects changes in refractive index (RI) at the sensor surface. RI changes as a consequence of binding events close to the sensor surface and are related to the increase of mass on the surface. An additional signal is obtained if the injected sample has a RI that differs from that of the running buffer. This signal is referred to as a solvent effect. When the solvent effect is small (in the order of 100 RU) it can normally be eliminated from the total signal by subtraction of the signal from the reference surface. However, the introduction of a high-RI solvent such as DMSO can give rise to large shifts in RI during the injection, and mere subtraction of the data from the reference flowcell is no longer sufficient. To correct for these effects a solvent calibration procedure is adopted. Buffer solutions with varying concentrations of solvent may be injected in sequence over reference and ligand bound surfaces. The responses of the calibration solutions, obtained from the reference surface, covers a typical range of −800 to +1200 RU relative to the baseline. A solvent correction curve is created by plotting the difference in response between ligand bound flow cells versus the response in the no ligand flow cell. This curve is used for correcting response levels obtained during sample injection.

Figure 1A:
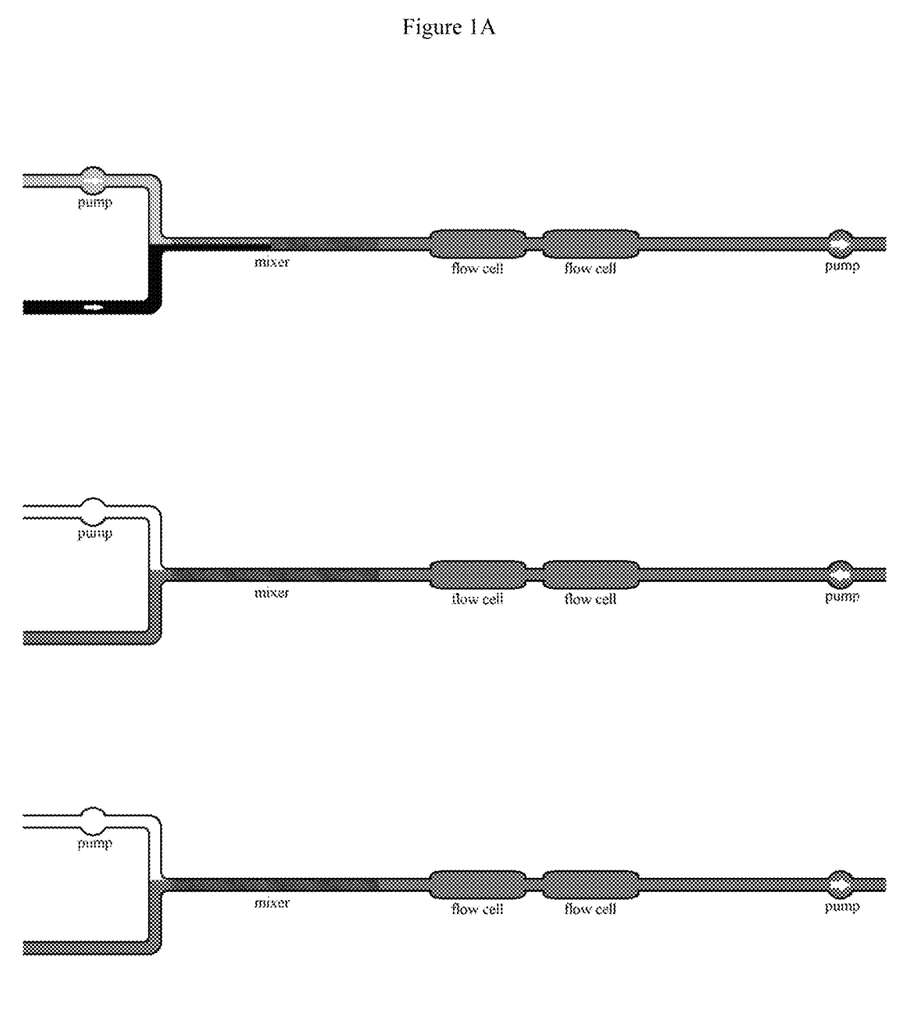

An illustrative embodiment of the invention is now described, using two pumps each on either side of the flow cell. FIG. 1A illustrates details of a portion of an IFC as two solutions move through the flow cells three times, showing the direction (arrows) and mixing pattern in the flow channel. Compared to a manual process, the user only needs to prepare 2 different solutions here. In the figure, the two solutions (dark and light shaded in the top channel) are mixed as illustrated by an intermediate shade as it passes through the flow cell (top channel). The motions of the solutions are indicated by arrows inside the channels. After a first pass, the solution is not mixed well enough to obtain a good solvent correction curve. Thus the flow of the solution is reversed in the middle channel to further mix the solution. Thus, the two upper parts of the drawing show the two passes of the solution over the flow cells. The third part shows an optional third pass. If needed, the second and third pass can be repeated to improve the mixing even more. In practice, two passes provides a sufficiently mixed solution for the generation of a good solvent correction curve.

Figure 3:
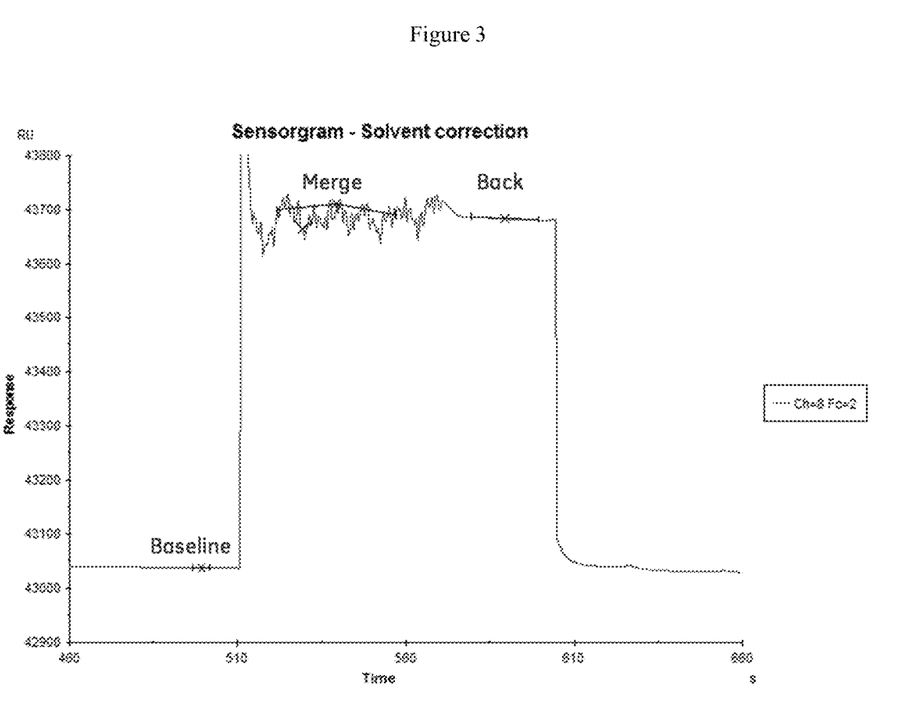
FIG. 3 shows a sensorgram of the data collected using an embodiment of the invention.

During the first pass the higher flow rate of one of the pumps is indicated by a wider arrow. The lower flow rate of the other pump and the resulting differential flow is indicated by more narrow arrows. If e.g. the flow rate of the second pump on the right of the flow cell is 10 μl/min and the flow rate of the first pump (on the left, for solution one) is 3 μl/min, there will be a resulting differential flow rate of solution two by 7 μl/min. The resulting mix ratio will be 30% solution one and 70% solution two. However, mixing is not complete as observed on a sensorgram (FIG. 3, Merge part). After the injection ends, the first pump can be stopped. By reversing the second pump, the injected solution can be sent back to the flow cells again. The solution now have had more time to get mixed by diffusion. The result is a more homogeneous solution the second time the solution passes the flow cells (FIG. 3 back part). While two flow cells are shown in the figure, it is merely an example only. In certain embodiments, a single flow cell may be present between the two pumps. Alternatively, more than two flow cells may be present between the two pumps.

Figure 1B:
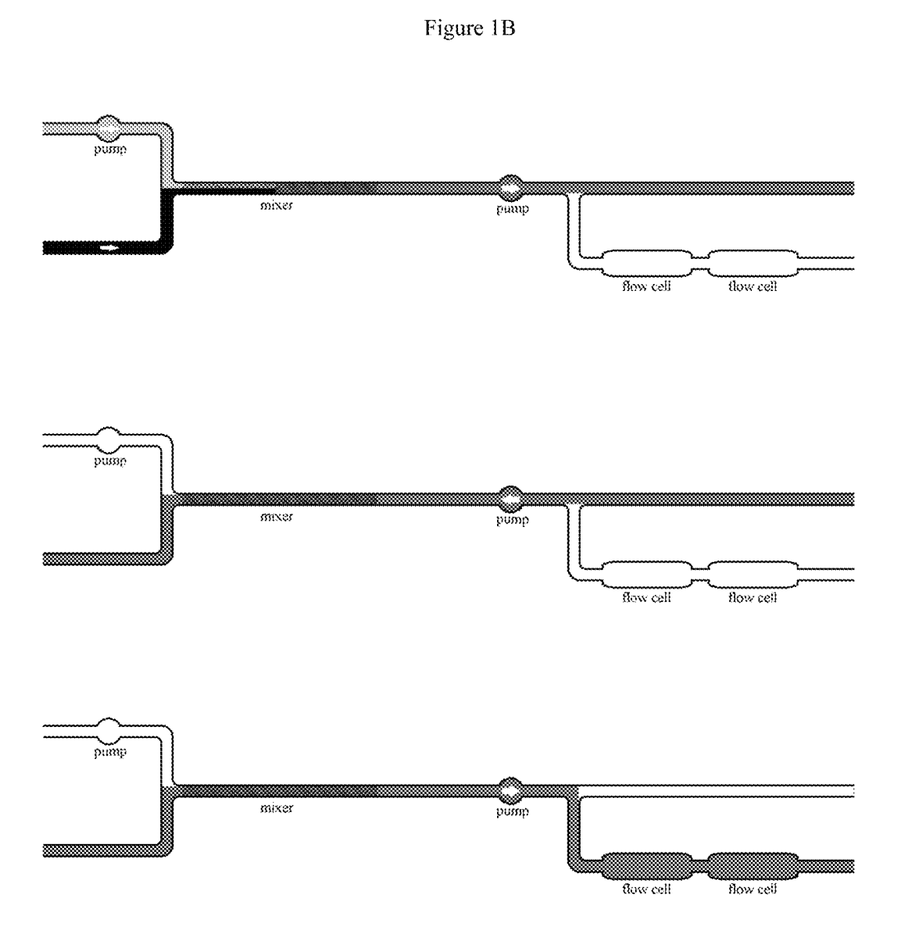

In alternative embodiments, pumping the mixed solution through channels and valves may also achieve the desired homogeneity of a mixed solution. FIG. 1B shows an alternative embodiment where the two pumps operate to mix the solution in a channel, and only the mixed solution is directed into the flow cell(s). FIG. 1B illustrates details of a portion of an IFC as two solutions move through the flow cells three times, showing the direction (arrows) and mixing pattern in the flow channel. In the figure, the two solutions (dark and light shaded in the top channel) are mixed as illustrated by an intermediate shade as it passes through the channel (top).

The motions of the solutions are indicated by arrows inside the channels. After a first pass, the solution is not mixed well enough to obtain a good solvent correction curve. Thus the flow of the solution is reversed in the middle channel to further mix the solution. The bottom part shows a third pass. During the first pass the higher flow rate of one of the pumps is indicated by a wider arrow. The lower flow rate of the other pump and the resulting differential flow is indicated by more narrow arrows. If e.g. the flow rate of the second pump on the right is 10 µl/min and the flow rate of the first pump (on the left, for solution one) is 3 µl/min, there will be a resulting differential flow rate of solution two by 7 µl/min. The resulting mix ratio will be 30% solution one and 70% solution two. After the injection ends, the first pump can be stopped. By reversing the second pump, the injected solution can be sent back again. The solution now have had more time to get mixed by diffusion. The result is a more homogeneous solution the second time the solution passes the channel, and an even better mixed solution when the solution passes through the channel a third time.

Alternatively, both pumps may be located at the channels at the left hand side of the drawings.

Figure 2:
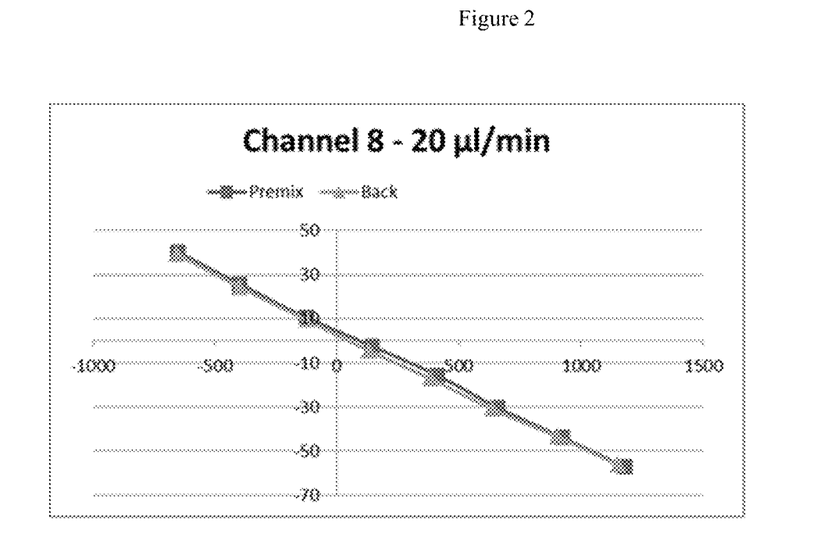
FIG. 2 shows solvent correction points produced with the invention (Back) compared with curve produced with manual mixing methodology (Premix).

Experiments performed show that a solvent correction curve produced this way (e.g., ligand-immobilized—reference response plotted against reference response and fitted to a $2^{nd}$ degree polynom) gives a curve that overlaps with a solvent correction curve from manually mixed solutions (FIG. 2), hence the manual and automatic method achieves same result, i.e., the correction are the same in both cases. In FIG. 2, the units for both x- and y-axis are both RU.

It is to be noted that the term "optical sensor surface" or "solid support" as used herein is to be interpreted broadly and is meant to comprise any solid (flexible or rigid) substrate onto which one or more binding agents can be immobilized and molecular interactions therewith be detected by the particular detection system chosen. The substrate may be biological, non-biological, organic, inorganic or a combination thereof, and may be in the form of particles, strands, precipitates, gels, sheets, tubings, spheres, containers, capillaries, pads, slices, films, plates, slides, etc, having any convenient shape, including disc, sphere, circle, etc. The substrate surface may have any two-dimensional configuration and may include, for example steps, ridges, kinks, terraces and the like and may be the surface of a layer of material different from that of the rest of the substrate. In certain embodiments, the optical sensor surface is part of a detector based upon evanescent wave sensing. Preferably, the optical sensor surface is part of a detector based upon surface plasmon resonance.

It may many times be convenient to carry out certain methods of the invention in a flow cell, e.g., of the type used in the above-mentioned Biacore® instruments. Other flow cells that may be used in the present invention are also well known to the skilled person and need not be described herein.

In another aspect, it is provided a method for mixing two liquids in a microchannel, comprising
  b. providing a first liquid comprising a specific composition and a second liquid comprising another composition;
  c. mixing the two liquids on line at a predetermined proportion in a micochannel; wherein mixing the two liquids comprises injecting the two liquids each at an individual, preset flow rate, let the combined liquid travel through the microchannel, and reverse the flow so that the combined liquid passes through the microchannel a second time.

In certain embodiments of the method for mixing two liquids, the flow may be reversed another time so that the combined liquid passes through the microchannel a third time.

In certain embodiments mixing the two liquids is realized by controlling flow rate for each liquid.

In certain embodiments the flow rates of the liquids are controlled by one or more pumps.

The effectiveness of liquid mixing may easily be assessed as long as the mixing is performed in connection to a detection spot, by assessing the smoothness as a parameter of mixing effectiveness (e.g. compare merge part with back part in FIG. 3).

The following general principles are applicable for certain aspects of the invention.

Surface binding interactions and bulk changes of refractive index may be characterized using a number of different interaction analysis techniques. Commercially available biosensors include the above-mentioned Biacore® system instruments, which are based on surface plasmon resonance (SPR) and permit monitoring of surface interactions in real time.

The phenomenon of SPR is well known. SPR arises when light is reflected under certain conditions at the interface between two media of different refractive indices, and the interface is coated by a metal film, typically silver or gold. In the Biacore® instruments, the media are the sample and the glass of a sensor chip that is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the Biacore® system the sample side.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the Biacore® system, the SPR response values are expressed in resonance units (RU). One RU represents a change of 0.00001° in the angle of minimum reflected light intensity, which for most proteins is roughly equivalent to a change in concentration of about 1 $pg/mm^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicated on the sensorgram by a drop in RU over time as analyte dissociates from the surface-bound ligand.

A detailed discussion of the technical aspects of the Biacore® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the Biacore® instruments may be found in U.S. Pat. No. 5,492,840. The full disclosures of the above-mentioned U.S. patents are incorporated by reference herein.

While the description above has been made with some respect to the Biacore® systems, it is understood that the invention may be used in connection with numerous other techniques for detecting binding interactions based on refractive index change and other physical phenomenon that also require solvent correction at the solid support surface. Real time detection systems are, however, preferred, especially those based on chemical sensor or biosensor technology.

A biosensor is broadly defined as a device that uses a component for molecular recognition (for example a layer with immobilized antibodies) in either direct conjunction with a solid state physicochemical transducer, or with a mobile carrier bead/particle being in conjunction with the transducer. While such sensors are typically based on label free techniques, detecting, e.g., a change in mass, refractive index, or thickness for the immobilized layer, there are also sensors relying on some kind of labelling. Typical sensor detection techniques include, but are not limited to, mass detection methods, such as optical, thermo-optical and piezoelectric or acoustic wave (including, e.g., surface acoustic wave (SAW) and quartz crystal microbalance (QCM)) methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) which may include scatter enhancing labels, optical wave guide sensors; external reflection imaging, evanescent wave-based imaging such as critical angle resolved imaging, Brewster angle resolved imaging, SPR angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

EXAMPLE

Surface Preparation:
A sensor chip CM5 was docked and 12000 RU human serum albumin was immobilized by amine coupling using amine coupling kit from GE Healthcare. 50 µg/ml human serum albumin in 10 mM Acetate pH 5.0 was injected for 7 minutes.
The buffers and solvent correction solutions were prepared as described below:
Stock solution 10×PBS-P+ (with 0.5% P20) provided by GE Healthcare was used to prepare running buffers.
1. Preparation of 2 litres 1.02×PBS-P+: 204 ml 10×PBS-P+ stock was diluted to 2000 ml with Milli-Q water. This buffer was used to prepare running buffer and solvent correction stock solutions.

2. Preparation of solvent correction stock solutions and assay running buffer: 10 ml of solvent correction stock solutions with 1.5% and 2.8% DMSO and 1 litre of assay running buffer with 2% DMSO were prepared according to Table 1.

TABLE 1

Solutions for solvent correction and 2% DMSO running buffer.

|  | 1.5% DMSO | 2.8% DMSO | 2.0 DMSO running buffer |
|---|---|---|---|
| 1.02 × PBS-P+ | 9.6 ml | 9.8 ml | 980 ml |
| 100% DMSO | 0.15 ml | 0.28 ml | 20 ml |
| Final volume | ~10 ml | ~10 ml | 1000 ml |

3. Preparation of solvent correction working solutions: Using the 1.5% and 2.8% DMSO stock solutions, a series of aliquots for the solvent correction curve, according to Table 2 (volumes given in µl) were prepared.

TABLE 2

Preparation of solvent correction solutions. Volumes given in µl.

| Buffer | Vial | | | | | | | |
|---|---|---|---|---|---|---|---|---|
|  | 1 | 2 | 3 | 4 | 5 | 6 | 7 | 8 |
| 1.5% DMSO | 0 | 200 | 400 | 600 | 800 | 1000 | 1200 | 1400 |
| 2.8% DMSO | 1400 | 1200 | 1000 | 800 | 600 | 400 | 200 | 0 |

4. These solutions 1-8 were injected one after the other over both flow-cells for the "Premix" data.
5. In the Merge-back experiment only solutions 1 and 8 were used but injected with different flow rates and mixed in the IFC as described above.
The results obtained using manual and merge-back injection are comparable, as illustrated in FIG. 2.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:
1. A method for establishing a solvent correction curve, comprising:
  a. providing a first solution and a second solution, the first solution having a higher concentration of the same organic solvent as the second solution;
  b. mixing the first solution and second solution at a predetermined proportion within a flow channel of an integrated microfluidic cartridge (IFC), the flow channel comprising a first flow cell with an optical sensor surface that is not immobilized with a ligand or analogue, wherein mixing the two solutions at the predetermined proportion is realized by merged inline injection using a first preset flow rate for the first solution and a second preset flow rate for the second solution and a ratio of the first preset flow rate and second preset flow rate results in the predetermined proportion giving a desired concentration and reversing the flow so that the mixed solution passes through the first flow cell at least a second time;

c. obtaining a sensorgram of the mixed solution from the optical sensor surface of step (b), the sensorgram comprising a report point;

d. mixing the first solution and second solution at the predetermined proportion as in step (b) in a flow channel of the integrated microfluidic cartridge (IFC), the flow channel comprising a second flow cell with an optical sensor surface that is immobilized with a ligand or analogue;

e. obtaining a sensorgram of the mixed solution from the optical sensor of step (d), the sensorgram comprising a report point;

f. repeat steps (b) and (c) n times each at a different, predetermined proportion of the two solutions; and g. establishing the solvent correction curve using the report points from steps (c) and (e);

wherein n is at least 3.

2. The method of claim 1, wherein mixing the two solutions comprises injecting the two solutions each at an individual, preset flow rate.

3. The method of claim 2, wherein the flow is reversed another time so that the combined solution passes through the flow cell(s) a third time.

4. The method of claim 1, wherein mixing the two solutions comprises injecting the two solutions each at an individual, preset flow rate, let the combined solution travel through a channel and/or valve, prior to entering the flow cell.

5. The method of claim 1, wherein the flow rates of the solutions are controlled by one or more pumps.

6. The method of claim 1, wherein the IFC comprises multiple, parallel channels.

7. The method of claim 1, wherein the organic solvent is DMSO.

8. A method for obtaining a corrected response of an analyte, comprising a. generating a sensorgram for a solution with the analyte in a flow cell including an optical sensor surface which contains immobilized partners for the analyte;

b. generating a sensorgram for said solution in the same or another flowcell having an optical sensor surface which does not contain immobilized partners for the analyte;

c. obtaining a corrected response by first, for each signal, deducting the signal of (b) from that of (a) to generate a modified sensorgram, followed by adjusting signals of the modified sensorgram or report points from the sensorgram according to the correction curve of claim 1.

9. The method of claim 8, wherein the analyte is a small molecule having a size of between about 80 to about 1000 Dalton.

10. The method of claim 8, wherein said optical sensor surface is part of a detector based upon evanescent wave sensing.

11. The method of claim 8, wherein said optical sensor surface is part of a detector based upon surface plasmon resonance.

12. The method of claim 1, wherein the IFC comprises a single channel where mixing in step (b) and (d) happen that also comprises the first flow cell with the optical sensor surface that is not immobilized with a ligand or analogue, and the second flow cell with the optical sensor surface that is immobilized with a ligand or analogue.

* * * * *